United States Patent [19]

Zentel et al.

[11] Patent Number: 5,616,573

[45] Date of Patent: Apr. 1, 1997

[54] GLUCOCORTICOIDS

[75] Inventors: Hans J. Zentel; Michael Töpert; Henry Laurent; Thomas Brumby; Peter Esperling, all of Berlin, Germany

[73] Assignee: Schering Aktiengesellschaft, Berlin, Germany

[21] Appl. No.: 530,352

[22] PCT Filed: Mar. 24, 1994

[86] PCT No.: PCT/EP94/00937

§ 371 Date: Oct. 6, 1995

§ 102(e) Date: Oct. 6, 1995

[87] PCT Pub. No.: WO94/22898

PCT Pub. Date: Oct. 13, 1994

[30] Foreign Application Priority Data

Apr. 7, 1993 [DE] Germany .................. 43 11 987.5

[51] Int. Cl.$^6$ .................. A61K 31/57; C07J 5/00
[52] U.S. Cl. .................. 514/172; 514/174; 514/176; 514/177; 514/178; 514/179; 514/180; 514/181; 540/63; 540/70; 540/110; 552/564; 552/565; 552/566; 552/570; 552/572; 552/573; 552/574; 552/576; 552/577; 552/588
[58] Field of Search .................. 552/564, 565, 552/566, 570, 572, 573, 574, 576, 577, 588; 540/63, 70, 110, 172, 174, 176, 177, 178, 179, 180, 181

[56] References Cited

FOREIGN PATENT DOCUMENTS

| 9310141 | 5/1993 | WIPO | C07J 5/00 |
| 9323040 | 11/1993 | WIPO | A61K 31/435 |
| 9323041 | 11/1993 | WIPO | A61K 31/435 |

*Primary Examiner*—Kimberly J. Prior
*Attorney, Agent, or Firm*—Millen, White, Zelano, & Branigan, P.C.

[57] ABSTRACT

Glucocorticoids of general formula I $$R-Val-O-GC \text{ (II)},$$

are described,
in which

O-GC is the radical of a 21-hydroxycorticoid that has an antiinflammatory action, Val represents a valine radical in the 21-position of the corticoid and R means a hydrogen atom or a hydrocarbon radical with up to 32 carbon atoms that is optionally substituted by hydroxy groups, amino groups, oxo groups and/or halogen atoms and/or interrupted by oxygen atoms, $SO_2$ groups and/or NH groups and their salts.

6 Claims, No Drawings

GLUCOCORTICOIDS

This application is a 371 of PCT/EP94/00937 filed Mar. 24, 1994.

The invention relates to glucocorticoids of general formula I

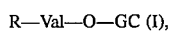
R—Val—O—GC (I), in which

O-GC is the radical of a 21-hydroxycorticoid that has an antiinflammatory action, Val represents a valine radical in the 21-position of the corticoid, and R means a hydrogen atom or a hydrocarbon radical with up to 32 carbon atoms that is optionally substituted by hydroxy groups, amino groups, oxo groups and/or halogen atoms and/or interrupted by oxygen atoms, $SO_2$ groups and/or NH groups and their salts.

The glucocorticoids according to the invention are valuable intermediate products and/or pharmacologically effective substances which are used, i.a., for the treatment of inflammatory conditions that are characterized by increased activity of the enzyme leukocyte-elastase.

Glucocorticoids are the best-known class of antiinflammatory active ingredients. Owing to their broad range of uses and their great antiinflammatory action, corticoid preparations are therapeutic agents of first choice in a wide variety of inflammatory diseases, such as, for example, diseases of the rheumatoid group, allergies, inflammatory diseases of the lungs, heart, and intestines, bronchial asthma, hyperproliferative diseases of the skin (psoriasis), eczemas, auto-immune diseases, or states of shock.

Their potential side effects, such as suppression of the brain-pituitary gland-suprarenal axis, their catabolic action, their influence on salt and water balance, osteoporosis, their influence on the blood-sugar level in the case of diabetics or the induction of skin atrophy in the case of topical application keep this class of substances from being put to an even broader range of therapeutic uses. According to present knowledge, these side effects, just like the antiinflammatory action of the glucocorticoids, are mediated by the same receptor. Up to now, therefore, reductions of the side-effect potential have been achieved by increasing the metabolic clearance of local-action corticoids (anti-drug principle). More lipophilic prodrugs are supposed to promote the penetration of corticoids into the skin and improve the retention of corticoids in the lungs. Despite the reduced side-effect potential of modern corticoids, especially long-term treatment with active ingredients of this class of substances remains critical.

Leukocyte-elastase is a serine-protease with a molecular weight of about 30,000 D. It is formed in promyelocytes and is found mainly in neutrophilic granulocytes [Duswald, K. H. (1983), Zur Pathobiochemie der Leukozyten-Elastase [Pathobiochemistry of Leukocyte-Elastase], GIT Verlag Ernst Giebler, Darmstadt.] Their occurrence is also described in Monozyten, Lymphozyten und eosinophilen Granulozyten [Monocytes, Lymphocytes and Eosinophilic Granulocytes] [Kargi et al. (1990)]. Elastase and Cathepsin G of Human Monocytes: Heterogeneity and Subcellular Localization to Peroxidase-Positive Granules. The Journal of Histochemistry and Cytochemistry 38: 1179–1186; Lungarella et al. (1992). Identification of Elastase in Human Eosinophils: Immunocalization, Isolation and Partial Characterization. Archives of Biochemistry and Biophysics, 292: 128–135; Bristow et al. (1991). Elastase is a constituent product of T cells. Biochemical and Biophysical Research Communications, 181: 232–239.] The enzyme is secreted in vitro after stimulation of granulocytes and monocytes [Schmidt (1978). Differential Release of Elastase and Chymotrypsin from Polymorphonuclear Leukocytes. In: Neutral Proteases of Human Polymorphonuclear Leukocytes. Havemann and Janoff (Editors) Urban & Schistzenberg, Inc. Baltimore, Munich; Xie et al. (1993). Release of Elastase from Monocytes Adherent to a Fibronectin-Gelatin Surface. Blood 81: 186–192.] High elastase activities are observed in vivo in the case of inflammatory diseases of the lungs, in the case of rhinitis, in synovial fluid in the case of rheumatoid arthritis, and on the skin surface in the case of different forms of eczema [Tanaka et al. (1990). A Sensitive and Specific Assay for Granulocyte Elastase in Inflammatory Tissue Fluid Using L-Pyroglutamyl-L-prolyl-L-valine-p-nitroanilide. Clinica Chimica Acta 187: 173–180; Wiedow et al. (1992). Lesional Elastase Activity in Psoriasis, Contact Dermatitis, and Atopic Dermatitis. Journal for Investigative Dermatology 99: 306–309.]. Elastase inhibitors are developed as therapeutic agents for the indication of pulmonary emphysema. Leukocyte-elastase cleaves ester and peptide bonds C-terminally of a short recognition sequence. The recognition sequence is readily characterized. The C-terminal radical plays a small role with regard to the catalytic activity of the enzyme [Castillo et al. (1979). Sensitive Substrates for Human Leukocyte and Porcine Pancreatic Elastase: A Study of the Merits of Various Chromophoric and Fluorogenic Leaving Groups In Assays for Serine Proteases. Analytical Biochemistry 99:53–64.]. The attempt to achieve an antiinflammatory action by inhibiting leukocyte-elastase is known.

It is also known that elastase transcortin cleaves the transport protein from physiological corticoids that have only a weak antiinflammatory action (hydrocortisone, corticosterone). The cleavage product of this protein has a significantly reduced affinity for the glucocorticoid. The hypothesis is based on the idea that an inflammation-specific release of corticoids could be produced by the activity of leukocyte-elastase [Hammond et al. (1990). A Role for Corticosteroid-Binding Globulin in Delivery of Cortisol to Activated Neutrophile. Journal of Clinical Endocrinology and Metabolism 71: 34–39; Hammond et al. (1990). Interaction Between Corticosteroid Binding Globulin and Activated Leukocytes in Vitro. Biochemical and Biophysical Research Communications 172: 172–177.]. The idea of using the enzymatic activity of leukocyte-elastase for inflammation-specific activation of inactive corticoid prodrugs is new. Such compounds could reduce the side-effect potential of glucocorticoids, e.g., in dermatological indications, diseases of the rheumatoid group or with use of glucocorticoids in inflammatory lung diseases.

The glucocorticoid prodrugs are cleaved into the effective glucocorticoid and the pharmacologically inactive peptide by the catalytic activity of leukocyte-elastase. In this way, the active glucocorticoid is released selectively at the focus of inflammation. This circumstance results in an increase of the concentration of the active glucocorticoid in the focus of inflammation. The concentrations of the active glucocorticoid in non-inflamed areas are thus kept to a minimum. As a result, a reduction in the local and systemic side-effect potential is achieved.

Glucocorticoid prodrugs according to the invention that can be used are, for example, those which are derivatives of 21-hydroxycorticoids, which are mentioned in EPA 0098 566 or the "Red List" [Herausg. Bundesverband der Pharmazeutischen Chemie e.V. [Editors Registered Association of Pharmaceutical Chemistry] Frankfurt and Main]. As radicals R of the prodrugs, for example, acyl radicals with 1 to 12 carbon atoms, benzyl radicals or those which, with the valine radical, form an oligopeptide radical with 2 to 6 amino acids, optionally provided with the usual protective groups, are considered.

Preferred oligopeptide radicals are those of aliphatic amino acids and especially those which contain alanine, proline, and valine as amino acids.

Suitable protective groups are, for example, those which are listed in volume XV/1 of "Methoden der Organischen Chemie [Methods of Organic Chemistry]" [Houben-Weyl, p. 20 ff].

Especially preferred glucocorticoids are those of general formula II according to the invention

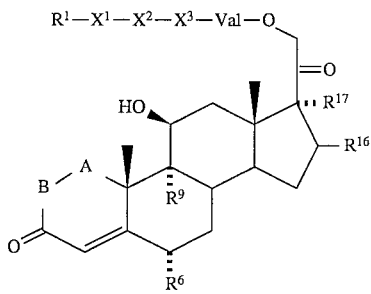

in which $R^1$=H, CH=O (C=O)R", (C=O)OR" or $SO_2R$"

$X^1$—$X^3$=independently of one another, alanine, proline or valine,

A-B=$CH_2$—$CH_2$ or CH=CH $R^6$=H, F, Cl, Me, $R^9$=H, F, Cl, $R^{16}$=H, Me, OH, $R^{17}$=H, OH, O(C=O)R''' or $R^{16}$, $R^{17}$=is alkylidenedioxy, in which R" represents a hydrocarbon radical that contains $C_1$–$C_{18}$ and R''' represents a $C_1$–$C_{10}$ alkyl (straight-chain or branched-chain) aryl, alkylaryl, or $C_1$–$C_3$ alkoxy radical and the alkylidene radical is derived from an aliphatic aldehyde that contains 1–6 C atoms, a ketone that contains 3–6 C atoms, or a cyclic ketone or benzaldehyde that contains 5–6 C atoms and their salts.

The preferred recognition sequence consists of $X^1$-$X^3$= independently of one another, alanine, proline or valine and especially of $X^1$, $X^2$=alanine, $X^3$=proline, valine. Any other tetrapeptide sequence, however, can also be used within the scope of the invention, if it bonds to elastase and is accepted as substrate.

Suitable hydrocarbon radicals R" and R''' are those which are derived from the already-mentioned protective groups.

The synthesis of the glucocorticoids according to the invention is done according to the processes that are familiar to one skilled in the art, as they are used in general in the case of peptide syntheses ("Methoden der Organischen Chemie" (Houben-Weyl, Vol. XV/1 and XV/2). The sample applications below are used to explain the invention in greater detail.

The abbreviations that are used are:

Aib=aminoisobutyric acid, Ala=alanine, Gly=glycine, Pro=proline, Val=valine; BMV=betamethasone-17-valerate, FC =fluocortolone, HC=hydrocortisone, MP=6α-methylprednisolone, MPP=6α-methylprednisolone-17-propionate, TCA=triamcinolone acetonide; Ac=acetyl, ASA=amino acid analysis, Boc=tertbutoxycarbonyl, Bz=benzoyl, Cbs=4-chlorobenzenesulfonyl, Cbp =3-(9-carbazolyl)-propionic acid, DDC=dicyclohexylcarbodiimide, DMAP=4-(N,N-dimethylamino)-pyridine, DPAc=diphenylacetyl, DPC= diphenylcarbamoyl, Fmoc=9-fluorenylmethoxycarbonyl, NCA=N-carbonic anhydrides, Piv=pivaloyl, Pht, phthyloyl, TFA=trifluoroacetic acid, Z=benzyloxycarbonyl.

The IUPAC recommendations for the naming of peptides [Biochem. J. 219, 345 (1984)] are observed in these sample applications.

EXAMPLES OF SYNTHESIS

Example 1

N-(1,1-Dimethylethoxycarbonyl)-valine [11β,21-dihydroxy-3,20-dioxo-6α-methyl-17-propionyloxy-pregna-1,4-dien-21-yl] ester (Boc-Val-O-MPP)

A solution of 2.15 g (5.00 mmol) of 6α-methylprednisolone-17-propionate in 25 ml of dichloromethane is mixed with 1.36 g (6.25 mmol) of N-(1,1-dimethylethoxycarbonyl)-valine and 121 mg (0.99 mmol) of 4-dimethylaminopyridine. Then, a solution of 1.36 g (6.59 mmol) of dicyclohexylcarbodiimide in 5 ml of dichloromethane is added in one shot. After 1–3 hours, the precipitate that is produced is suctioned off and washed with diethyl ether. The filtrate is concentrated by evaporation in a vacuum. Chromatography on silica gel (hexane→hexane/ethyl acetate 1:1) provides 3.01 g (96%) of N-(1,1-dimethyloxycarbonyl)-valine [11β, 21-dihydroxy-3,20-dioxo-6α-methyl-17-propionyloxy-pregna-1,4-dien-21-yl] ester. Crystallization from dichloromethane/diisopropyl ether. Melting point 110°–130° C. $[α]_D$=+32° (chloroform).

Example 2

Valine [11β,21-dihydroxy-3,20-dioxo-6α-methyl-17-propionyloxy-pregna-1,4-dien-21-yl] ester trifluoroacetate (H-Val-O-MPP-TFA)

Under initial cooling, 5 ml of trifluoroacetic acid is poured over 896 mg (1.42 mmol) of N-(1,1-dimethylethoxycarbonyl)valine [11β,21-dihydroxy-3,20-dioxo-6α-methyl-17-propionyloxy-pregna-1,4-dien-21-yl] ester, and it is stirred for 1–2 hours at room temperature. Then, the trifluoroacetic acid is evaporated in a vacuum. The residue is taken up in a little dichloromethane, 5 ml of toluene is added and then evaporated to dryness in a vacuum. The residue is crystallized. 728 mg (80%) of valine [11β,21-dihydroxy-3,20-dioxo-6α-methyl-17-propionyloxy -pregna-1,4-dien-21-yl] ester trifluoroacetate is obtained. Melting point 148° C.

Example 3

N-(N-(N-(1,1-Dimethylethoxycarbonyl)-L-alanyl)-L-alanyl)-L -prolyl)-L-valine [11β,21-dihydroxy-3,20-dioxo-6α-methyl-17-propionyloxy-pregna-1,4-dien-21-yl] ester (Boc-Ala-Ala-Pro-Val-O-MPP) (Boc-Ala-Ala-Pro-Val-O-MPP)

336 mg (0.52 mmol) of valine [11β,21-dihydroxy-3,21-dioxo -6α-methyl-17-propionyloxy-pregna-1,4-dien-21-yl] ester trifluoroacetate, 180 mg (0.50 mmol) of N-(1,1-dimethylethoxycarbonyl)-alanyl-alanyl-proline, 68 mg (0.50 mmol) of hydroxybenzotriazole are dissolved in 20 ml of dichloromethane, and 150 mg (0.72 mmol) of dicyclohexylcarbodiimide in 2 ml of dichloromethane is added. Then, 55 ml (0.50 mmol) of N-methylmorpholine is immediately added and stirred for 2 hours at room temperature. For working-up, it is filtered off from dicyclohexylurea, rewashed with diethyl ether and the combined organic phases are washed with 40 ml of 0.5N HCl, 0.5N NaOH and saturated sodium chloride solution in each case and dried on sodium sulfate. Evaporation of the solvent in a vacuum yields the crude product. Chromatography on silica gel (hexane→hexane/acetone 1:1) yields 402 mg (89%) of N-(N-(N-(N-(1,1-dimethylethoxycarbonyl)-L -alanyl)-L-alanyl)-L-prolyl)-L-valine [11β,21-dihydroxy-3,20-dioxo-6α-methyl-17-propionyloxy-pregna-1,4-dien-21-yl] ester, crystallization from dichloromethane/diisopropyl ether/hexane.

Melting point sintering starting from 135° C., decomposition starting from 160° C., $[\alpha]_D = -28°$ (c=0.5% in chloroform), HPLC: 99%, ASA: Ala 20.4 Pro 0.95 Val 1.01, racemic test (GC): D-Ala<1% D-Pro<1% D-Val<1%.

Example 4

N-(N-(N-(N-(9H-Fluoren-9-ylmethoxycarbonyl)-L-alanyl)-L-alanyl) -L-prolyl)-L-valine [11β,21-dihydroxy-3,20-dioxo-6α-methyl-17-propionyloxy-pregna-1,4-dien-21-yl] ester (Fmoc-Ala-Ala-Pro-Val -O-MPP)

As described in Example 3, 631 mg (0.98 mmol) of valine [11β,21-dihydroxy-3,21-dioxo-6α-methyl-17-propionyloxy-pregna -1,4-dien-21-yl] ester trifluoroacetate, 446 mg (0.93 mmol) of N-(9H-fluoren-9-ylmethoxycarbonyl)-alanyl-alanyl-proline, 136 mg (1.00 mmol) of hydroxybenzotriazole, 215 mg (1.04 mmol) of dicyclohexylcarbodiimide and 220 ml (2.00 mmol) of N-methylmorpholine are reacted. Chromatography on silica gel (dichloromethane→dichloromethane/methanol 97:3) yields 400 mg (42%) of N-(N-(N-(N-(9H-fluoren-9-ylmethoxycarbonyl)-L-alanyl)-L -alanyl)-L-prolyl)-L-valine [11β,21-dihydroxy-3,20-dioxo-6α-methyl-17-propionyloxy-pregna-1,4-dien-21-yl ] ester. Crystallization from dichloromethane/diisopropyl ether/hexane.

$[\alpha]_D = -24°$ (c=0.5% in chloroform), HPLC: 98%.
Racemic test (GC): D-Ale<1% D-Pro<1% D-Val<1%

Example 5

N-(N-(N-(N-(Phenylmethoxycarbonyl)-L-alanyl)-L-alanyl)-L-prolyl) -L-valine [11β21-dihydroxy-3,20-dioxo-6α-methyl-17-propionyloxy -pregna-1,4-dien-21-yl] ester (Z-Ala-Ala-Pro-Val-O-MPP)

Under the conditions indicated in Example 3, 131 mg (0.20 mmol) of valine [11β,21-dihydroxy-3,21-dioxo-6α-methyl-17-propionyloxy-pregna-1,4-dien-21-yl] ester trifluoroacetate, 72 mg (0.19 mmol) of N-(benzyloxycarbonyl)-alanyl-alanyl-proline (Z-Ala-Ala-Pro-OH), 51 mg (0.37 mmol) of hydroxybenzotriazole, 46 mg (0.22 mmol) of dicyclohexylcarbodiimide and 30 ml (0.28 mmol) of N-methylmorpholine are reacted. Gradient chromatography on silica gel (dichloromethane→dichloromethane/methanol 9:1) provides 101 mg (60%) of N-(N-(N-(N-(phenylmethoxycarbonyl)-L -alanyl)-L-alanyl)-L-prolyl)-L-valine [11β,21-dihydroxy-3,20-dioxo-6α-methyl-17-propionyloxy-pregna-1,4-dien-21-yl] ester.

Crystallization from methanol/diisopropyl ether.

Melting point starting from 137° C. (dec.), $[\alpha]_D = -23°$ (c=0.5% in chloroform), HPLC: 98–99%.

Racemic test (GC): D-Ala 1.8% D-Pro<1% D-Val<1%.

Example 6

N-(N-(N-(L-alanyl)-L-alanyl)-L-prolyl)-L-valine [11β,21-dihydroxy-3,20-dioxo-6α-methyl-17-propionyloxy-pregna-1,4-dien-21-yl] ester trifluoroacetate (H-Ala-Ala-Pro-Val-O-MPP-TFA)

3.5 g (4.0 mmol) of Boc-Ala-Ala-Pro-Val-O-MPP (Example 3) is dissolved in 50 ml of dichloromethane and mixed with 6.5 ml of trifluoroacetic acid at 0° C. After 2.5 hours, the solvent is removed i.vac. (5 HPA), the residue is taken up in dichloromethane and precipitated with diisopropyl ether. 3.5 g (99%) of N-(N-(N-(L-alanyl)-L-alanyl)-L-prolyl)-L-valine [11β,21-dihydroxy-3,20-dioxo-6α-methyl-17 -propionyloxy-pregna-1,4 -dien-21-yl] ester trifluoroacetate is obtained.

Melting point 164°–178° C. (dec), $[\alpha]_D = -19°$ (c=0.5% in chloroform) , HPLC: 98%

ASA: Ala 1.93 Pro 1.09 Val 0.98, racemic test (GC): D-Ala <1% D-Pro<1% D-Val<1%.

Example 7

N-(N-(N-(N-(Methylcarbonyl)-L-alanyl)-L-alanyl)-L-prolyl)-L-valine [11β,21-dihydroxy-3,20-dioxo-6α-methyl-17-propionyloxy -pregna-1,4-dien-21-yl] ester (Ac-Ala-Ala-Pro-Val-O-MPP)

500 mg (0.57 mmol) of H-Ala-Ala-Pro-Val-O-MPP x TFA (Example 3) is dissolved in 20 ml of dichloromethane, mixed with 115 μl (1.21 mmol) of acetic anhydride and stirred for 24 hours at room temperature. The residue that remains after removal of the solvent i.vac. is chromatographed (200 g of silica gel 60, dichloromethane→dichloromethane/methanol 9:1) 344 mg (75%) of N-(N-(N-(N-(methylcarbonyl)-L-alanyl)-L-alanyl)-L-prolyl)-L-valine [11β,21-dihydroxy-3,20-dioxo-6α-methyl-17-propionyloxy -pregna-1,4-dien-21-yl] ester, and, after recrystallization, 305 mg (66%) in crystalline form from methanol/diisopropyl ether/hexane are obtained.

Melting point 152°–155° C. sintering: 174° C., $[\alpha]_D = -28°$ (c=0.5% in chloroform), HPLC: 98–99%.

Racemic test (GC): D-Ala 2.3% D-Pro<1% D-Val<1%.

Example 8

N-(N-(N-(N-(Phenylcarbonyl)-L-alanyl)-L-alanyl)-L-prolyl)-L-valine [11β,21-dihydroxy-3,2 0-dioxo-6α-methyl-17-propionyloxy -pregna-1,4-dien-21-yl] ester (Bz-Ala-Ala-Pro-Val-O-MPP)

250 mg (0.28 mmol) of H-Ala-Ala-Pro-Val-O-MPP x TFA (Example 3) is dissolved in 50 ml of dichloromethane and 5 ml of triethylamine, mixed with 49 μl (0.37 mmol) of benzoyl chloride and stirred for 28 hours at room temperature. For working-up, it is washed with water and saturated sodium chloride solution, dried on sodium sulfate and concentrated by evaporation i.vac. The residue that remains after removal of the solvent i.vac. is chromatographed. Gradient chromatography on 200 g of silica gel 60 (acetone/hexane 1:2→2:1) yields 153 mg (62%) of N-(N-(N-(N-(phenylcarbonyl) -L-alanyl)-L-alanyl)-L-prolyl)-L-valine [11β,21-dihydroxy-3,20-dioxo-6α-methyl-17-propionyloxy-pregna-1,4-dien -21-yl] ester, and, after recrystallization, 131 mg (53%) in crystalline form from dichloromethane/diisopropyl ether.

Melting point starting from 150° C. decomposition $[\alpha]_D = -14°$ (c=0.5% in chloroform), HPLC: 95–98%.

Racemic test (GC): D-Ala 5.0% D-Pro<1% D-Val<1%.

Example 9

N-(N-(N-(N-(Valeroyl)-L-alanyl)-L-alanyl)-L-prolyl)-L-valine [11β,21-dihydroxy-3,20-dioxo-6α-methyl-17-propionyloxy-pregna -1,4-dien-21-yl] ester (Valeroyl-Ala-Ala-Pro-Val-O-MPP)

307 mg (0.35 mmol) of H-Ala-Ala-Pro-Val-O-MPP x TFA (Example 3), 36 µl (0.33 mmol) of valeric acid, 52 mg (0.35 mmol) of N-hydroxy-benzotriazole and 74 µl (0.66 mmol) of N-methylmorpholine are dissolved in 40 ml of dichloromethane, mixed with a solution of 84 mg (0.41 mmol) of dicyclohexylcarbodiimide in 10 ml of dichloromethane and stirred for 4 hours at room temperature. For working-up, the precipitated urea is filtered off, the filtrate is diluted with 40 ml of dichloromethane and washed with 40 ml each of 0.5N NaOH, 0.5N HCl and saturated sodium chloride solution, dried on sodium sulfate and concentrated by evaporation i.vac. The residue that remains after removal of the solvent i.vac. is chromatographed. Gradient chromatography on 200 g of silica gel 60 (dichloromethane→dichloromethane/methanol 95:5) yields 180 mg (64%) of N-(N-(N-(N -(valeroyl)-L-alanyl)-L-alanyl)-L-prolyl)-L-valine [11β,21-dihydroxy-3,20-dioxo-6α-methyl-17-propionyloxy-pregna-1,4-dien -21-yl] ester and, after recrystallization, 157 mg (56%) in crystalline form from dichloromethane/diisopropyl ether/hexane.

Melting point 142° C., $[\alpha]_D = -54°$ (c=0.5% in methanol), HPLC: 94–98%.

Racemic test (GC): D-Ala 1.7% D-Pro<1% D-Val<1%.

Example 10

N-(N-(N-(N-((Diphenylmethyl)carbonyl)-L-alanyl)-L-alanyl)-L -prolyl)-L-valine [11β,21-dihydroxy-3,20-dioxo-6α-methyl-17-propionyloxy-pregna-1,4-dien-21-yl] ester (DPAc-Ala-Ala-Pro-Val -O-MPP)

150 mg (0.17 mmol) of H-Ala-Ala-Pro-Val-O-MPP x TFA (Example 3), 40 mg (0.19 mmol) of diphenylacetic acid, 23 mg (0.17 mmol) of N-hydroxy-benzotriazole and 41 µl (0.66 mmol) of diisopropylethylamine are dissolved in 3 ml of dichloromethane, mixed with a solution of 69 mg (0.33 mmol) of dicyclohexylcarbodiimide in 4 ml of dichloromethane and stirred for 23 hours at room temperature. For working-up, the precipitated urea is filtered off and the residue that remains after removal of the solvent i.vac. is chromatographed (gradient chromatography, 24 g of silica gel 60, hexane→hexane/acetone 1:2). 148 mg (91%) of N-(N-(N-(N-((diphenylmethyl)carbonyl)-L -alanyl)-L-alanyl)-L-prolyl)-L-valine [11β,21-dihydroxy-3,20-dioxo-6α-methyl-17-propionyloxy-pregna-1,4-dien-21-yl] ester is obtained, which is purified again on a Lichroprep Si60A prepacked column (hexane→hexane/dichloromethane/methanol 30:60:10) (86 mg ⁀ 53%) and 75 mg (46%) of crystalline compound from dichloromethane/diisopropyl ether is obtained.

Melting point sintered starting from 157° C., 177° C., HPLC: 99%.

ASA: Ala 1.90 Pro 1.10 Val 1.00, racemic test (GC): D-Ala 2.9% D-Pro 2.1% D-Val 0.8%.

Example 11

N-(N-(N-(N-(Diphenylcarbamoyl)-L-alanyl)-L-alanyl)-L-prolyl)-L-valine [11β,21-dihydroxy-3,20-dioxo-6α-methyl-17-propionyloxy -pregna-1,4-dien-21-yl] ester (DPC-Ala-Ala-Pro-Val-O-MPP)

150 mg (0.17 mmol) of H-Ala-Ala-Pro-Val-O-MPP x TFA (Example 3) and 150 µl (0.89 mmol) of diisopropylethylamine are dissolved in 6 ml of dichloromethane, mixed with 155 mg (0.37 mmol) of diphenylcarbamoyl chloride and stirred for 110 hours at room temperature. The residue that remains after removal of the solvent i.vac. is chromatographed. Gradient chromatography (Lichroprep Si60A prepacked column, hexane→hexane/dichloromethane/methanol 30:60:10) yields 158 mg (97%) of N-(N -(N-(N-(diphenylcarbamoyl)-L-alanyl)-L-alanyl)-L-prolyl)-L-valine [11β,21-dihydroxy-3,20-dioxo-6α-methyl-17-propionyloxy-pregna -1,4-dien-21-yl] ester, and after recrystallization, 112 mg (68%) in crystalline form from dichloromethane/diisopropyl ether.

Melting point 150°–152° C., HPLC: 95.6–98.2%, racemic test (GC): D-Ala 2.9% D-Pro 2.0% D-Val<1%.

Example 12

N-(N-(N-(N-(2-Naphthoyl)-L-alanyl)-L-alanyl)-L-prolyl)-L-valine [11β,21-dihydroxy-3,20-dioxo-6α-methyl-17-propionyloxy-pregna -1,4-dien-21-yl] ester (2-Naphthoyl-Ala-Ala-Pro-Val-O-MPP)

120 mg (0.14 mmol) of H-Ala-Ala-Pro-Val-O-MPP x TFA (Example 3), 28 mg (0.16 mmol) of 2-naphthoic acid, 19 mg (0.14 mmol) of N-hydroxy-benzotriazole and 100 µl (0.57 mmol) of diisopropylethylamine are dissolved in 3 ml of dichloromethane, mixed with a solution of 67 mg (0.33 mmol) of dicyclohexylcarbodiimide in 1 ml of dichloromethane and stirred for 18 hours at room temperature. For working-up, the precipitated urea is filtered off and the residue that remains after removal of the solvent i.vac. is chromatographed (gradient chromatography on 23 g of silica gel 60, acetone/hexane 1:1→2:3). 103 mg (82%) of N-(N-(N-(N-(2-naphthoyl)-L-alanyl)-L -alanyl)-L-prolyl)-L-valine [11β,21-dihydroxy-3,20-dioxo-6α-methyl-17-propionyloxy-pregna-1,4-dien-21-yl] ester and, after recrystallization, 87 mg (69%) in crystalline form from dichloromethane/diisopropyl ether are obtained.

Melting point 166°–170° C., HPLC: 97.6–97.9%, ASA: Ala 1.90 Pro 1.12 Val 0.98, racemic test (GC): D-Ala 7.3% D-Pro 2.0% D-Val 0.8%.

Example 13

N-(N-(N-(N-(3-Phenyl-butenoyl)-L-alanyl)-L-alanyl)-L-prolyl)-L-valine [11β,21-dihydroxy-3,20-dioxo-6α-methyl-17-propionyloxy -pregna-1,4-dien-21-yl] ester (Cinnamoyl-Ala-Ala-Pro-Val-O-MPP)

120 mg (0.14 mmol) of H-Ala-Ala-Pro-Val-O-MPP x TFA (Example 3), 24 mg (0.16 mmol) of cinnamic acid, 19 mg (0.14 mmol) of N-hydroxy-benzotriazole and 100 µl (0.57 mmol) of diisopropylethylamine are dissolved in 3.5 ml of dichloromethane, mixed with a solution of 67 mg (0.33 mmol) of dicyclohexylcarbodiimide in 0.5 ml of dichloromethane and stirred for 64 hours at room temperature. For working-up, the precipitated urea is filtered off, and the residue that remains after removal of the solvent i.vac. is chromatographed (23 g of silica gel 60, dichloromethane/acetone/hexane 1:1:1→acetone/hexane 2:1). 98 mg (80%) of N-(N-(N-(N-(3-phenyl -butenoyl)-L-alanyl)-L-alanyl)-L-prolyl)-L-valine [11β,21-dihydroxy-3,20-dioxo-6α-methyl-17-propionyloxy-pregna-1,4-dien -21-yl] ester, and, after recrystallization, 81 mg (66%) of crystalline compound from ethyl acetate/hexane are obtained.

Melting point sintering starting from 154°, melt at 191° C., HPLC: 97.2–97.9%, ASA: Ala 1.89 Pro 1.13 Val 0.98, racemic test (GC): D-Ala 10.2% D-Pro 3.6% D-Val 2.5%.

Example 14

N-(N-(N-(N-(4-Chlorobenzenesulfonyl)-L-alanyl)-L-alanyl)-L -prolyl)-L-valine [11β,21-dihydroxy-3,20-dioxo-6α-methyl-17-propionyloxy-pregna-1,4-dien-21-yl] ester (Cbs -Ala-Ala-Pro-Val-O-MPP)

100 mg (0.11 mmol) of H-Ala-Ala-Pro-Val-O-MPP x TFA (Example 3) and 300 µl (1.71 mmol) of diisopropylethylamine are dissolved in 5 ml of tetrahydrofuran, mixed with 238 mg (1.13 mmol) of 4-chlorobenzenesulfonic acid chloride and stirred for 23 hours at room temperature. The residue that remains after removal of the solvent i.vac. is chromatographed. Gradient chromatography on 25 g of silica gel 60 (hexane/acetone 2:1→1:2) yields 75 mg (70%) of N-(N-(N-(N-(4-chlorobenzenesulfonyl)-L-alanyl)-L-alanyl)-L -prolyl)-L-valine [11β,21-dihydroxy-3,20-dioxo-6α-methyl-17-propionyloxy-pregna-1,4-dien-21-yl] ester, and, after recrystallization from dichloromethane/diisopropyl ether, 47 mg (44%) of crystalline product.

Melting point sintering starting from 151°, melt at 195° C., HPLC: 97.2–98.0%, ASA: Ala 1.60 Pro 1.28 Val 1.12, racemic test (GC): D-Ala 2.8% D-Pro 1.2% D-Val 0.8%[[]jf44a Example 15

N-(N-(N-(N-(2,2-Dimethylpropionyl)-L-alanyl)-L-alanyl)-L-prolyl) -L-valine [11β,21-dihydroxy-3,20-dioxo-6α-methyl-17-propionyloxy -pregna-1,4-dien-21-yl] ester (Piv-Ala-Ala-Pro-Val-O-MPP)

150 mg (0.17 mmol) of H-Ala-Ala-Pro-Val-O-MPP x TFA (Example 3) and 60 µl (0.34 mmol) of diisopropylethylamine are dissolved in 6 ml of dichloromethane, mixed with 20 µl (0.18 mmol) of pivaloyl chloride and stirred for 25 hours at room temperature. The residue that remains after removal of the solvent i.vac. is directly chromatographed. Gradient chromatography (24 g of silica gel 60, hexane→ hexane/acetone 7:3) yields 102 mg (70%) of slightly contaminated N-(N-(N-(N-(2,2-dimethylpropionyl)-L -alanyl)-L-alanyl)-L-prolyl)-L-valine [11β,21-dihydroxy-3,20-dioxo-6α-methyl-17-propionyloxy-pregna-1,4-dien-21-yl] ester. A second chromatography (Lichroprep Si60A prepacked column, hexane/dichloromethane 1:1→hexane/dichloromethane/methanol 30:60:10) yields 92 mg, 83 mg of crystalline compound consisting of dichloromethane/diisopropyl ether.

Sintered starting from 157° C. melting point 177° C. HPLC: 98.7%, ASA: Ala 1.90 Pro 1.10 Val 1.00, racemic test (GC): D-Ala 2.6% D-Pro 1.8% D-Val 0.6%.

Example 16

N-(N-(N-(N-(3-(Carbazol-9-yl)-propionyl)-L-alanyl)-L-alanyl)-L -prolyl)-L-valine [11β,21-dihydroxy-3,20-dioxo-6α-methyl-17-propionyloxy-pregna-1,4-dien-21-yl] ester (Cbp-Ala-Ala-Pro-Val -O-MPP)

150 mg (0.17 mmol) of H-Ala-Ala-Pro-Val-O-MPP x TFA (Example 3), 61 mg (0.26 mmol) of carbazolepropionic acid, 35 mg (0.26 mmol) of N-hydroxy-benzotriazole and 122 µl (070 mmol) of diisopropylethylamine are dissolved in 5 ml of dichloromethane, mixed with 65 mg (0.34 mmol) of ethyl-3(dimethylamino)propylcarbodiimide (EDC) and stirred for 67 hours at room temperature. For working-up, the solvent is removed i.vac. and the residue that remains is chromatographed (23 g of silica gel 60, acetone/hexane 1:9→1:1). 140 mg (83%) of N-(N-(N-(N-(3-(carbazol-9-yl)-propionyl)-L-alanyl)-L-alanyl)-L-prolyl)-L-valine [11β,21-dihydroxy-3,20-dioxo-6α-methyl-17-propionyloxy-pregna -1,4-dien-21-yl] ester, and, after recrystallization,, 99 mg (59%) in crystalline form from acetone/hexane are obtained.

Melting point sintering starting from 158°, melt at 182° C., HPLC: 95.8–96.3%, racemic test (GC): D-Ala 2.0% D-Pro 2.1% D-Val 1.4%.

Example 17

N-(N-(N-(N-(Phthaloyl)-glycyl)-L-alanyl)-L-alanyl)-L-prolyl) -L-valine [11β,21-dihydroxy-3,20-dioxo-6α-methyl-17-propionyloxy -pregna-1,4-dien-21-yl] ester (Pth-Gly-Ala-Ala-Pro-Val-O-MPP)

120 mg (0.14 mmol) of H-Ala-Ala-Pro-Val-O-MPP x TFA (Example 3), 31 mg (0.15 mmol) of phthaloylglycine, 20 mg (0.15 mmol) of N-hydroxy-benzotriazole and 48 µl (0.27 mmol) of diisopropylethylamine are dissolved in 2 ml of dichloromethane, mixed with a solution of 56 mg (0.27 mmol) of dicyclohexylcarbodiimide in 1 ml of dichloromethane and stirred for 17 hours at room temperature. For working-up, the precipitated urea is filtered off and the residue that remains after removal of the solvent i.vac. is chromatographed (gradient chromatography, 25 g of silica gel 60, hexane/acetone 1:1→1:2). 68 mg (52%) of N-(N-(N-(N-(N-(phthaloyl)-glycyl)-L-alanyl)-L -alanyl)-L-prolyl)-L-valine [11β,21-dihydroxy-3,20-dioxo-6α-methyl-17-propionyloxy-pregna-1,4-dien-21-yl] ester and from this, 66 mg (51%) of crystalline product from dichloromethane/diisopropyl ether are obtained.

Melting point (dec.) with gas generation starting from 165° C., HPLC: 97.2–98.4, ASA: Ala 1.89 Pro 1.12 Val 0.99, racemic test (GC): D-Ala 1.1% D-Pro 0.8% D-Val 0.8% Gly identified.

Example 18

N-(N-(N-(N-(N-((9H-Fluoren-9-ylmethoxy)carbonyl)-2-amino-2-methyl-propionyl)-L-alanyl)-L-alanyl)-L-prolyl)-L-valine [11β,21-dihydroxy-3,20-dioxo-6α-methyl-17-propionyloxy-pregna-1,4-dien -21-yl] ester (Fmoc-Aib-Ala-Ala-Pro-Val-O-MPP)

200 mg (0.14 mmol) of H-Ala-Ala-Pro-Val-O-MPP x TFA (Example 3), 120 mg (0.34 mmol) of Fmoc-Aib-NCA and 200 µl (1.14 mmol) of diisopropylethylamine are dissolved in 10 ml of dichloromethane and stirred for 23 hours at room temperature. For working-up, the solvent is removed i.vac. and the residue that remains is chromatographed (gradient chromatography, 25 g of silica gel 60, hexane→hexane/acetone 1:2). 135 mg (55%) of N-(N-(N-(N-(N -((9H-fluoren-9-ylmethoxy)carbonyl)-2-amino-2-methyl-propionyl)-L -alanyl)-L-alanyl)-L-prolyl)-L-valine [11β,21-dihydroxy-3,20-dioxo-6α-methyl-17-propionyloxy-pregna-1,4-dien-21-yl] ester, and, after recrystallization, 102 mg (44%) after crystallization from dichloromethane/diisopropyl ether that is repeated twice are obtained.

$[\alpha]_D$=−23° (c=0.26% in chloroform), HPLC: 97–98%. Racemic test (GC): D-Ala 1.4% D-Pro 1.4% D-Val 1.7% Aib identified.

Example 19

N-(1,1-Dimethylethoxycarbonyl)-valine [11β,17,20-trihydroxy-3,20-dioxo-6α-methyl-pregna-1,4-dien-21-yl] ester (Boc-Val-O-MP)

Analogously to Example 1, 1.94 g of 6e-methylprednisolone, 1.37 g of N-(1,1-dimethylethoxycarbonyl)-valine, 74 mg of 4-dimethylaminopyridine and 1.34 g of dicyclohexylcarbodiimide in 30 ml of dichloromethane/dioxane 1:1 are reacted. Chromatography on silica gel (dichloromethane→ dichloromethane/acetone 3:1) yields 2.58 g (87%) of N-(1, 1-dimethylethoxycarbonyl)-valine [11β,17,20-trihydroxy-3, 20-dioxo-6α-methyl-pregna-1,4-dien-21-yl] ester. Crystallization from dichloromethane/diisopropyl ether.

Melting point 144°–148° C. $[\alpha]_D$=+70° (chloroform).

Example 20

Valine [11β,17,20-trihydroxy-3,20-dioxo-6α-methyl-pregna-1,4-dien-21-yl] ester trifluoroacetate (H-Val-O-MP TFA)

806 mg of N-(1,1-dimethylethoxycarbonyl)-valine [11β,17,20-trihydroxy-3,20-dioxo-6α-methyl-pregna-1,4-dien-21-yl] ester (Example 19) is reacted under the conditions described in Example 2. 616 mg (75%) of valine [11β,17,20-trihydroxy-3,20-dioxo-6α-methyl-pregna-1,4-dien-21-yl] ester trifluoroacetate is obtained.

Melting point 167°–171° C. (decomposition). $[\alpha]_D=+95°$ (methanol).

Example 21

N-(N-(N-(N-(1,1-Dimethylethoxycarbonyl)-L-alanyl)-L-alanyl)-L-prolyl)-L-valine [11β,17,21-trihydroxy-3,20-dioxo-6α-methyl-pregna-1,4-dien-21-yl] ester (Boc-Ala-Ala-Pro-Val-O-MP)

Under the conditions indicated in Example 3, 1.44 g (2.46 mmol) of valine [11β, 17,20-trihydroxy-3,20-dioxo-6α-methyl-pregna-1,4-dien-21-yl] ester trifluoroacetate, 800 mg (2.24 mmol) of N-(1,1-dimethylethoxycarbonyl)-alanyl-alanyl-proline, 300 mg (2.24 mmol) of hydroxybenzotriazole, 555 mg (2.69 mmol) of dicyclohexylcarbodiimide and 0.49 ml (4.48 mmol) of N-methylmorpholine are reacted. Chromatography on silica gel (dichloromethane→dichloromethane/methanol 95:5) provides 1.54 g (77%) of N-(N-(N-(1,1-dimethylethoxycarbonyl)-L-alanyl)-L-alanyl)-L-prolyl)-L-valine [11β,17,21-trihydroxy-3,20-dioxo-6α-methyl-pregna-1,4-dien-21-yl] ester. Crystallization from dichloromethane/diisopropyl ether.

Melting point 155°–175° C., decomposition with gas generation, $[\alpha]_D=-2°$ (c=0.5% in chloroform), HPLC: 96.5–97.5%. Racemic test (GC): D-Ala 3.2% D-Pro 2.3% D-Val 1.9%. Cld: C 63.53 H 7.93 N 6.89 Fnd: C 63.52 H 7.70 N 6.97

Example 22

N-(N-(N-(N-((9H-Fluoren-9-yl-methoxycarbonyl)-L-alanyl)-L-alanyl)-L-prolyl)-L-valine [11β,17,21-trihydroxy-3,20-(dioxo-6α-methyl-pregna-1,4-dien-21-yl] ester (Fmoc-Ala-Ala-Pro-Val-O-MP)

510 mg (0.87 mmol) of valine [11β,17,20-trihydroxy-3,20-dioxo-6α-methyl-pregna-1,4-dien-21-yl] ester trifluoroacetate, 347 mg (0.72 mmol) of Fmoc-Ala-Ala-Pro-OH and 97 mg (0.72 mmol) of N-hydroxybenzotriazole are added to this sequence in 25 ml of dichloromethane, dissolved with 160 μl (1.45 mmol) of N-methylmorpholine. Then, a solution of 298 mg (1.45 mmol) of dicyclohexylcarbodiimide in 5 ml of dichloromethane is mixed and stirred for 5 hours at room temperature After cooling to −20° C. it is suctioned off from precipitated urea, washed with diethyl ether, the combined filtrates are extracted with 2×50 ml of 0.5N HCl, 0.5N NaOH each, washed with saturated sodium chloride solution and dried on sodium sulfate. The residue that remains after removal of the solvent i.vac. is directly chromatographed (110 g of silica gel, dichloromethane→dichloromethane/methanol 9:1). 478 mg (71%) of N-(N-(N-(N-((9H-fluoren-9-yl-methoxycarbonyl)-L-alanyl)-L-alanyl)-L-prolyl)-L-valine [11β,17,21-trihydroxy-3,20-dioxo-6α-methyl-pregna-1,4-dien-21-yl] ester is obtained. Crystallization from dichloromethane/diisopropyl ether yields 449 mg.

Melting point 169°–171° C., $[\alpha]_D=-2°$ (c=0.5% in chloroform), HPLC: 96.1–96.8%. Racemic test (GC): D-Ala 2.5% D-Pro>1% D-Val 1.4%. Cld: C 68.07 H 7.11 N 5.99 O 18.82 Fnd: C 67.95 H 7.54 N 5.68 O 18.74

Example 23

N-(N-(N-(L-Alanyl)-L-alanyl)-L-prolyl)-L-valine [11β,17,21-trihydroxy-3,20-dioxo-6α-methyl-pregna-1,4-dien-21-yl] ester hydrochloride (H-Ala-Ala-Pro-Val-O-MP x HCl)

939 mg (1.15 mmol) of Boc-Ala-Ala-Pro-Val-O-MP (Example 21) is dissolved in 10 ml of dioxane and 10 ml of HCl (4N in dioxane) is added. After 18 hours at room temperature, the solvent is removed i.vac., the residue is pulverized with dichloromethane, suctioned off and the obtained crystals are recrystallized from methanol/diisopropyl ether. 835 mg (94%) of N-(N-(N-(L-alanyl)-L-alanyl)-L-prolyl)-L-valine [11β,17,21-trihydroxy-3,20-dioxo-6α-methyl-pregna-1,4-dien-21-yl] ester hydrochloride is obtained.

Melting point starting from 200° C. (dec), $[\alpha]_D=-10°$ (c=0.5% in methanol), HPLC: 97%, racemic test (GC): D-Ala 2.7% D-Pro 1.7% D-Val >1%.

Example 24

N-(N-(N-(N-(Phenylcarbonyl)-L-alanyl)-L-alanyl)-L-prolyl)-L-valine [11β,17,21-trihydroxy-3,20-dioxo-6α-methyl-pregna-1,4-dien-21-yl] ester (Bz-Ala-Ala-Pro-Val-O-MP)

370 mg (0.46 mmol) of Boc-Ala-Ala-Pro-Val-O-MP (Example 21) is dissolved in 3 ml of dioxane and 4 ml of HCl (4N in dioxane) is added. After 16 hours at room temperature, the solvent is removed i.vac., dissolved in 4 ml of dichloromethane, mixed with 175 μl (1.00 mmol) of diisopropylethylamine and 58 μl (0.50 mmol) of benzoyl chloride and stirred for 17 hours at room temperature. For working-up, the solvent is removed i.vac. and the residue that remains is crystallized from dichloromethane/diisopropyl ether. 139 mg( 37% ) of N-(N-(N-(N-(phenylcarbonyl)-L-alanyl)-L-alanyl)-L-prolyl)-L-valine [11β,17,21-trihydroxy-3,20-dioxo-6α-methyl-pregna-1,4-dien-21-yl] ester is obtained.

HPLC: 97.1–97.7%, racemic test (GC): D-Ala 3.8% D-Pro 2.7% D-Val 2.6%.

Example 25

N-(N-(N-(N-((Phenylmethoxy)carbonyl)-L-alanyl)-L-alanyl)-L-prolyl)-L-valine [11β,17,21-trihydroxy-3,20-dioxo-6α-methyl-pregna-1,4-dien-21-yl] ester (Z-Ala-Ala-Pro-Val-O-MP)

200 mg (0.27 mmol) of H-Ala-Ala-Pro-Val-O-MP x HCl (Example 23) and 37 μl (0.27 mmol) of triethylamine are dissolved in 10 ml of dichloromethane, mixed with 42 μl (0.30 mmol) of benzyl chloroformate and stirred for 36 hours at room temperature. For working-up, it is diluted with 20 ml of dichloromethane and washed with 2N potassium hydrogen sulfate solution and saturated sodium chloride solution, dried on sodium sulfate and concentrated by evaporation i.vac. The residue that remains after removal of the solvent i.vac. is chromatographed. Gradient chromatography on 110 g of silica gel 60 (dichloromethane→dichloromethane/methanol 9:1) yields 156 mg (69%) of N-(N-(N-(N -((phenylmethoxy)-carbonyl)-L-alanyl)-L-alanyl)-L-prolyl)-L-valine [11β,17,21-trihydroxy-3,20-dioxo-6α-methyl-pregna-1,4-dien-21-yl] ester and, after recrystallization, 123 mg (54%) in crystalline form from methanol/diisopropyl ether.

HPLC: 98.7–99.7%, ASA: Ala 2.00 Pro 1.01 Val 0.99, racemic test (GC): D-Ala 2.2% D-Pro <1% D-Val 1.1%.

Example 26

N-(N-(N-(N-(Valeroyl)-L-alanyl)-L-alanyl)-L-prolyl)-L-valine [11β,17,21-trihydroxy-3,20-dioxo-6α-methyl-pregna-1, 4-dien-21-yl] ester (Valeroyl-Ala-Ala-Pro-Val-O-MP)

200 mg (0.27 mmol) of H-Ala-Ala-Pro-Val-O-MP x HCl 41c 33 µl (0.30 mmol) of valeric acid, 41 mg (0.30 mmol) of N-hydroxybenzotriazole and 66 µl (0.60 mmol) of N-methylmorpholine are dissolved in 20 ml of dichloromethane, mixed with a solution of 123 mg (0.60 mmol) of dicyclohexylcarbodiimide in 5 ml of dichloromethane and stirred for 105 hours at room temperature. For working-up, the precipitated urea is filtered off and the filtrate is concentrated by evaporation i.vac. Gradient chromatography of the amount of raw material of 110 g of silica gel 60 (hexane→hexane/acetone 6:4) yields 139 mg (65%) of N-(N -(N-(N-(valeroyl)-L-alanyl)-L-alanyl)-L-prolyl)-L-valine [11β,17, 21-trihydroxy-3,20-dioxo-6α-methyl-pregna-1,4-dien-21-yl] ester, 74 mg (35%) in crystalline form from methanol/ diisopropyl ether.

HPLC: 96.3–97.0%, racemic test (GC): D-Ala 2.5% D-Pro 2.4% D-Val<1%.

ZK 162494 AZ 204436 ON 128

Example 27

(2S)-2-((1,1-Dimethylethoxycarbonyl)-amino)-3-methyl-butyric acid [11β,17,21-trihydroxy-3,20-dioxo-pregn-4-en-21-yl] ester (Boc -Val-O-HC)

A solution of 3.63 g (10 mmol) of hydrocortisone in 150 ml of dichloromethane is mixed with 2.34 g (10.8 mmol) of N-(tert -butoxycarbonyl)-valine, 500 mg (4.1 mmol) of 4-dimethylaminopyridine and 3.1 g (15 mmol) of dicyclohexylcarbodiimide. The solution is stirred for 3 hours at room temperature, the precipitate that is produced is suctioned off and washed with dichloromethane. The filtrate is concentrated by evaporation in a vacuum. The chromatography on silica gel (hexane→hexane/ethyl acetate 1:1) provides 2.87 g (51%) of (2S)-2-((1,1-dimethylethoxycarbonyl)-amino)-3-methylbutyric acid [11β,17,21-trihydroxy-3, 20-dioxo-pregn-4-en-21-yl] ester. Crystallization from dichloromethane/diisopropyl ether.

Melting point 169° C., $[\alpha]_D$=+97° (chloroform).

Example 28

(2S)-2-Amino-3-methyl-butyric acid [11β,17,21-trihydroxy-3,20-dioxo-pregn-4-en-21-yl] ester trifluoroacetate (H-Val-O-HC-TFA)

500 mg (0.89 mmol) of (2S)-2-((1,1-dimethylethoxycarbonyl) -amino)-3-methyl-butyric acid [11β,17,21-trihydroxy-3,20-dioxo -pregn-4-en-21-yl] ester (Example 27) is mixed with 1 ml of trifluoroacetic acid and stirred for 10 minutes at room temperature. Then, the trifluoroacetic acid is evaporated in a vacuum. The residue is mixed with stirring with a little diethyl ether, the white precipitate that is produced is suctioned off and dried. 385 mg (76%) of (2S)-2-amino-3-methyl-butyric acid [11β,17,21-trihydroxy-3,20-dioxo-pregn-4-en-21-yl] ester trifluoroacetate is obtained.

Melting point 188° C.

Example 29

N-(N-(N-(N-(9H-Fluoren-9-yl-methoxycarbonyl)-L-alanyl)-L-alanyl) -L-prolyl)-L-valine [11β,17,21-trihydroxy-3, 20-dioxo-pregn-4-en -21-yl] ester (Fmoc-Ala-Ala-Pro-Val-O-HC)

A solution of 350 mg (0.62 mmol) of (2S)-2-amino-3-methylbutyric acid [11β,17,21-trihydroxy-3,20-dioxo-pregn-4-en-21-yl] ester trifluoroacetate (Example 28) in 30 ml of dichloromethane is mixed with 350 mg (0.73 mmol) of N-(9-fluorenylmethoxycarbonyl)-alanyl-alanyl-proline, 100 mg (0.74 mmol) of hydroxybenzotriazole, 150 mg (0.72 mmol) of dicyclohexylcarbodiimide and 0.07 ml (0.63 mmol) of N-methylmorpholine, and it is stirred for 2 hours at room temperature. For working-up, it is filtered off from dicyclohexylurea, rewashed with diethyl ether. The combined organic phases are washed with 50 ml of 0.5N HCl, 0.5N NaOH and saturated sodium chloride solution in each case and dried on sodium sulfate. Evaporation of the solvent in a vacuum yields the crude product. The chromatography on silica gel (hexane→hexane/acetone 1:1) yields 405 mg (72%) of N-(N-(N-(N-(9H -fluoren-9-yl-methoxycarbonyl)-L-alanyl)-L-alanyl)-L-prolyl)-L-valine [11β,17,21-trihydroxy-3,20-dioxo-pregn-4-en-21-yl] ester.

Crystallization from hexane/ethyl acetate.

Melting point 193° C.

Example 30

(2S)-2-((1,1-Dimethylethoxycarbonyl)-amino)-3-methyl-butyric acid [11β,21-dihydroxy-6α-fluoro-16α-methyl-3, 20-dioxo-pregna-1,4-dien-21-yl] ester (Boc-Val-O-FC)

26 mmol of fluocortolone (FC) is reacted with 32 mmol of Boc-valine (Boc-Val-OH), 2.9 mmol of 4-dimethylaminopyridine and 34 mmol of dicyclohexylcarbodiimide in dichloromethane/dioxane 3:2. Chromatography (ethyl acetate/hexane 2:1): F$_1$ 9.3 g of pure product, F$_2$ 4.8 g of slightly contaminated product. (Total yield 92%) crystallization of F$_1$ from ethyl acetate/hexane yields 7.0 g (46%) of (2S)-2-((1,1-dimethylethoxycarbonyl)-amino)-3-methyl-butyric acid [11β,21-dihydroxy-6α-fluoro-16α-methyl-3, 20-dioxo-pregna-1,4-dien-21-yl] ester.

Melting point 166°–168° C., $[\alpha]_D$=+85° (c=0.55 in chloroform) . Cld: C 66.88 H 7.89 N 2.44 F 3.31 Fnd: C 66.90 H 7.82 N 2.73 F 3.29

Example 31

(2S)-2-Amino-3-methyl-butyric acid [11β,21-dihydroxy-6α-fluoro -16α-methyl-3,20-dioxo-pregna-1,4-dien-21-yl] ester trifluoroacetate (H-Val-O-FC x TFA)

6.4 g (11 mmol) of Boc-Val-O-FC (Example 29) is reacted with trifluoroacetic acid/dichloromethane analogously to Example 2. Crystallization from dichloromethane/diisopropyl ether (ultrasonic bath) yields 5.6 g (86%) of (2S)-2-amino-3-methylbutyric acid [11β,21-dihydroxy-6α-fluoro-16α-methyl-3,20-dioxo -pregna-1,4-dien-21-yl] ester trifluoroacetate.

Melting point 135°–138° C.

Example 32

N-(N-(N-(N-((1,1-Dimethyl)-ethoxycarbonyl)-L-alanyl)-L-alanyl)-L -prolyl)-L-valine [6α-fluoro-11β,21-dihydroxy-16α-methyl-3,20dioxo-pregna-1,4-dien-21-yl] ester (Boc-Ala-Ala-Pro-Val-O-FC)

884 mg (1.50 mmol) of H-Val-O-FC x TFA (Example 31), 500 mg (1.40 mmol) of Boc-Ala-Ala-Pro-OH and 168 mg (1.40 mmol) of N-hydroxybenzotriazole are dissolved in this sequence in 50 ml of dichloromethane and 330 µl (3.00 mmol) of N-methylmorpholine is added. Then, a solution of 289 mg (1.40 mmol) of dicyclohexylcarbodiimide in 2 ml of dichloromethane is added and stirred for 2 hours at room temperature. Then, it is suctioned off from precipitated urea, the filtrate is concentrated by evaporation and filtered again. Chromatography of this amount of raw material (300 g of silica gel, hexane/acetone 1:1) yields 861 mg (76%) of N-(N-(N-(N-((1,1-dimethyl) ethoxycarbonyl) -L-alanyl) -L- alanyl)-L-prolyl)-L-valine [6α-fluoro-11β,21-dihydroxy-16α-methyl-3,20-dioxo-pregna-1,4-dien-21-yl] ester. 737 mg of pure product is obtained [one or more words missing] recrystallization from dichloromethane/diisopropyl ether.

Melting point starting from 136° C. decomposition $[\alpha]_D$= 0° (c=0.5% in chloroform), HPLC: 98%. Racemic test (GC): D-Ala 3.0% D-Pro 1.9% D-Val<1%.

Example 33

N-(N-(N-(9H-Fluoren-9-yl-methoxycarbonyl)-L-alanyl)-L-alanyl) -L-prolyl)-L-valine [6α-fluoro-11β,21-dihydroxy-16α-methyl-3,20-dioxo-pregna-1,4-dien-21-yl]-pregna-1,4-dien-21-yl] ester (Fmoc -Ala-Ala-Pro-Val-O-FC)

442 mg (0.75 mmol) of H-Val-O-TCA x TFA (Example 31), 336 mg (0.70 mmol) of Fmoc-Ala-Ala-Pro-OH and 84 mg (0.70 mmol) of N-hydroxybenzotriazole are dissolved in this sequence in 20 ml of dichloromethane, and 155 μl (1.50 mmol) of N-methylmorpholine is added. Then, a solution of 145 mg (0.70 mmol) of dicyclohexylcarbodiimide in 2 ml of dichloromethane is added and stirred for 6 hours at room temperature. Then, it is suctioned off from precipitated urea, the filtrate is concentrated by evaporation and filtered again. Chromatography of this amount of raw material (300 g of silica gel, dichloromethane→dichloromethane/acetone 1:1) yields 298 mg (=44%) of N-(N-(N-(N -(9H-fluoren-9-yl-methoxycarbonyl)-L-alanyl)-L-alanyl)-L-prolyl) -L-valine [6α-fluoro-11β,21-dihydroxy-16α-methyl-3,20-dioxo -pregna-1,4-dien-21-yl]-pregna-1,4-dien-21-yl] ester. Recrystallization from dichloromethane/diisopropyl ether yields 158 mg of pure substance. This material also contained several contaminants and is further purified by HPLC (Novapak, MeCN/10 mmol of ammonium hydrogen carbonate 60:40).

Melting point starting from 158° C. decomposition, $[\alpha]_D$= +1° (c=0.5% in chloroform), HPLC: 99%. Racemic test (GC): D-Ala 1.0% D-Pro 1.4% D-Val 3.5%.

Example 34

N-(N-(N-(L-Alanyl)-L-alanyl)-L-prolyl)-L-valine [6α-fluoro -11β,21-dihydroxy-16α-methyl-3,20-dioxo-pregna-1,4-dien-21-yl]-pregna-1,4-dien-21-yl] ester hydrochloride (H-Ala-Ala-Pro-Val-O-FC x HCl)

113 mg (0.14 mmol) of Boc-Ala-Ala-Pro-Val-O-FC (Example 32) is dissolved in 1 ml of hydrochloric acid dioxane (4N HCl in dioxane). After 6 hours at room temperature, the solvent is removed i.vac., the residue is recrystallized from dichloromethane/diisopropyl ether. 117 mg (>100%) of N-(N-(N -(L-alanyl)-L-alanyl)-L-prolyl)-L-valine [6α-fluoro-11β,21-dihydroxy-16α-methyl-3,20-dioxopregna-1,4-dien-21-yl]-pregna -1,4-dien-21-yl] ester hydrochloride is obtained.

HPLC: 98.3–99.3%, racemic test (GC): D-Ala 6.4% D-Pro 3.4% D-Val 1.5%.

Example 35

N-(N-(N-(N-(Phenylcarbonyl)-L-alanyl)-L-alanyl)-L-prolyl)-L-valine [6α-fluoro-11β,21-dihydroxy-16α-methyl-3,20-dioxo-pregna -1,4-dien-21-yl]-pregna-1,4-dien-21-yl] ester (Bz-Ala-Ala-Pro -Val-O-FC)

105 mg (0.13 mmol) of H-Ala-Ala-Pro-Val-O-FC x HCl (Example 34) is dissolved in 3 ml of dichloromethane and 3 ml of triethylamine, mixed with 23 μl (0.20 mmol) of benzoyl chloride and stirred for 8 hours at room temperature. For working-up, it is washed with 1N HCl and water, dried on sodium sulfate and concentrated by evaporation i.vac. The residue that remains after removal of the solvent i.vac. is directly chromatographed. Gradient chromatography on 50 g of silica gel 60 (dichloromethane →dichloromethane/methanol 95:5) yields 96 mg (84%) of N-(N-(N -(N-(phenylcarbonyl)-L-alanyl)-L-alanyl)-L-prolyl)-L-valine [6α-fluoro-11β,21-dihydroxy-16α-methyl-3,20-dioxo-pregna-1,4-dien-21-yl]-pregna-1,4-dien-21-yl] ester, 75 mg (66%) yields 36 mg of pure compound after recrystallization from dichloromethane/diisopropyl ether.

HPLC: 96.1–96.9%, racemic test (GC): D-Ala 8.1% D-Pro<1% D-Val 1.4%.

Example 36

(2S)-2-((1,1-Dimethylethoxycarbonyl)-amino)-3-methyl-butyric acid [11β,21-dihydroxy-3,20-dioxo-9-fluoro-16β-methyl-17-valeroyloxy -pregna-1,4-dien-21-yl] ester (Boc-Val-O-BMV)

21 mmol of betamethasone-17-valerate is reacted with 25 mmol of Boc-valine (Boc-Val-OH), 2.5 mmol of 4-dimethylaminopyridine and 27 mmol of dicyclohexylcarbodiimidazole in dichloromethane/dioxane 1:1 analogously to Example 1. Chromatography (1. ethyl acetate/hexane 2:1 and 2. ethyl acetate/hexane 1:1) yields 10.1 g (73%) of pure (2S)-2-((1,1-dimethylethoxycarbonyl)-amino)-3-methyl-butyric acid [11β,21 -dihydroxy-3,20-dioxo-9-fluoro-16β-methyl-17-valeroyloxy-pregna -1,4-dien-21-yl] ester as foam.

$[\alpha]_D$=+51° (c=0.5% in chloroform). Cld: C 65.86 H 7.92 N 2.08 F 2.82 Fnd: C 65.53 H 7.72 N 2.24 F 2.69

Example 37

(2S)-2-Amino-3-methyl-butyric acid [11β,21-dihydroxy-3,20-dioxo -9-fluoro-16β-methyl-17-valeroyloxy-pregna-1,4-dien-21-yl] ester trifluoroacetate (H-Val-O-BMV x TFA)

8.5 g (13 mmol) of Boc-Val-O-BMV (Example 36) is reacted with trifluoroacetic acid/dichloromethane analogously to Example 2. The compound is not crystalline and is further used as crude product. C-NMR corresponds to the expected structure.

Example 38

N-(N-(N-(N-((1,1-Dimethyl)ethoxycarbonyl)-L-alanyl)-L-alanyl)-L -prolyl)-L-valine [9α-fluoro-11β,21-dihydroxy-16β-methyl-3,20-dioxo-17-valeroyloxy-pregna-1,4-dien-21-yl] ester (Boc-Ala-Ala -Pro-Val-O-BMV)

1.04 g (1.50 mmol) of H-Val-O-BMV x TFA (Example 37), 500 mg (1.40 mmol) of Boc-Ala-Ala-Pro-OH and 168 mg (1.40 mmol) of Nhydroxybenzotriazole are dissolved in this sequence in 50 ml of dichloromethane, and 330 μl (3.00 mmol) of N-methylmorpholine is added. Then, a solution of 289 mg (1.40 mmol) of dicyclohexylcarbodiimide in 2 ml of dichloromethane is added and stirred for 20 hours at room temperature. Then, it is suctioned off from precipitated urea, the filtrate is concentrated by evaporation and filtered again. Chromatography of this amount of raw material (300 g of silica gel, hexane/acetone 1:1) yields 806 mg( 63% ) of N-(N-(N-(N-((1,1-dimethyl)ethoxycarbonyl)-L-alanyl) -L-alanyl)-L-prolyl)-L-valine [9α-fluoro-11β,21-dihydroxy-16β-methyl-3,20-dioxo-17-valeroyloxy-pregna-1,4-dien-21-yl ] ester. Crystallization from dichloromethane/diisopropyl ether 542 mg (42%).

Melting point starting from 137° C. decomposition, $[\alpha]_D$=0° C. (c=0.5% in chloroform), HPLC: 98.1–99.2%. Racemic test (GC): D-Ala 2.1% D-Pro 2.2% D-Val 0.6%.

Example 39

N-(N-(N-(9H-Fluoren-9-yl-methoxycarbonyl)-L-alanyl)-L-alanyl) -L-prolyl)-L-valine [9α-fluoro-11β,21-dihydroxy-16β-methyl-3,20-dioxo-17-valeroyloxy-pregna-1,4-dien-21-yl] ester (Fmoc-Ala-Ala -Pro-Val-O-BMV)

689 mg (1.00 mmol) of H-Val-O-BMV x TFA (Example 37), 384 mg (0.80 mmol) of Fmoc-Ala-Ala-Pro-OH and 96 mg (0.80 mmol) of N-hydroxybenzotriazole are dissolved in this sequence in 20 ml of dichloromethane, and 155 µl (1.50 mmol) of N-methylmorpholine is added. Then, a solution of 145 mg (0.70 mmol) of dicyclohexylcarbodiimide in 2 ml of dichloromethane is added and stirred for 6 hours at room temperature. Then, it is suctioned off from precipitated urea, the filtrate is concentrated by evaporation and filtered again. The obtained solution is diluted with dichloromethane, extracted with 0.5N NaOH and 0.5N HCl, dried on sodium sulfate and concentrated by evaporation i.vac. Chromatography of the amount of raw material (300 g of silica gel, dichloromethane/acetone 1:1) yields 232 mg (28%) of N-(N-(N -(N-(9H-fluoren-9-yl-methoxy-carbonyl)-L-alanyl)-L-alanyl)-L -prolyl)-L-valine [9α-fluoro-11β,21-dihydroxy-16β-methyl-3,20-dioxo-17-valeroyloxy-pregna-1,4-dien-21-yl] ester, and, after crystallization from dichloromethane/diisopropyl ether, 200 mg of pure product.

Melting point starting from 143° C. decomposition, $[\alpha]_D=$ −13° (c=0.5% in chloroform), HPLC: 95.4–99%. ASA: Ala 1.98 Pro 0.99 Val 1.03, racemic test (GC): D-Ala 8.0% D-Pro 4.7% D-Val 2.6%.

Example 40

N-(N-(N-(L-Alanyl)-L-alanyl)-L-prolyl)-L-valine [9α-fluoro -11β,21-dihydroxy-16β-methyl-3,20-dioxo-17-valeroyloxy-pregna-1,4-dien-21-yl] ester hydrochloride (H-Ala-Ala-Pro-Val-O-BMV x HCl)

137 mg (0.15 mmol) of Boc-Ala-Ala-Pro-Val-O-BMV (Example 38) is dissolved in 1 ml of hydrochloric acid dioxane (4N HCl in dioxane). After 6 hours at room temperature, the solvent is removed i.vac. and the residue is recrystallized from dichloromethane/diisopropyl ether. 114 mg (89%) of N-(N-(N-(L -alanyl)-L-alanyl)-L-prolyl)-L-valine [9α-fluoro-11β,21-dihydroxy 16β-methyl-3,20-dioxo-17-valeroyloxy-pregna-1,4-dien-21-yl] ester hydrochloride is obtained.

HPLC: 97.0–99.2%, racemic test (GC): D-Ala 4.9% D-Pro 3.8% D-Val 1.1%.

Example 41

N-(N-(N-(N-(Phenylcarbonyl)-L-alanyl)-L-alanyl)-L-prolyl)-L-valine [9α-fluoro-11β,21-dihydroxy-16β-methyl-3, 20-dioxo-17-valeroyloxy-pregna-1,4-dien-21-yl] ester (Bz-Ala-Ala-Pro-Val-O-BMV)

102 mg (0.12 mmol) of H-Ala-Ala-Pro-Val-O-BMV x HCl 40 c is dissolved in 3 ml of dichloromethane, mixed with 21 µl (0.18 mmol) of benzoyl chloride and 356 µl (2.50 mmol) of diisopropylethylamine and stirred for 5 hours at room temperature. For working-up, it is washed with 1N HCl and water, dried on sodium sulfate and concentrated by evaporation i.vac. The residue that remains after removal of the solvent i.vac. is directly chromatographed. Gradient chromatography on 50 g of silica gel 60 (dichloromethane→dichloromethane/methanol 95:5) yields 79 mg (72%) of N-(N-(N-(N-(phenylcarbonyl)-L -alanyl)-L-alanyl)-L-prolyl)-L-valine [9α-fluoro-11β,21-dihydroxy -16β-methyl-3,20-dioxo-17-valeroyloxy-pregna-1,4-dien-21-yl] ester and, after recrystallization, 56 mg (51%) of crystalline product from ethyl acetate/hexane.

HPLC: 95% racemic test (GC): D-Ala 12.1% D-Pro 3.1% D-Val 1.4%.

Example 42

(2S)-2-((1,1-Dimethylethoxycarbonyl)-amino)-3-methyl-butyric acid [11β,21-dihydroxy-3,20-dioxo-9-fluoro-16α, 17-[(1-methylethylidene)bis(oxy)]-pregna-1,4-dien-21-yl] ester (Boc -Val-O-TCA)

11 mmol of triamcinolone-acetonide (TCA) is reacted with 13 mmol of Boc-valine (Boc-Val-OH), 1.2 mmol of DMAP and 14 mmol of DCC in dichloromethane/dioxane 1:1 analogously to Example 1. Chromatography (ethyl acetate/hexane 2:1) yields 3.72 g (53%) of (2S)-2-((1,1-dimethyloxycarbonyl)-amino)-3-methyl-butyric acid [11β,21-dihydroxy-3,20-dioxo-9-fluoro-16α,17-[(1-methylethylidene)bis(oxy)]-pregna-1,4-dien-21-yl] ester. Repeated crystallization from ethyl acetate/hexane provides 5.52 g (52%) of pure product.

Melting point 238–240° C., $[\alpha]_D=+75°$ (c=0.5% in chloroform) . Cld: C 64.54 H 7.49 N 2.21 F 3.00 Fnd: C 64.23 H 7.21 N 2.35 F 2.88

Example 43

(2S)-2-Amino-3-methyl-butyric acid [11β,21-dihydroxy-3, 20-dioxo -9-fluoro-16α,17-[(1-methylethylidene)bis(oxy)]-pregna-1,4-dien -21-yl] ester trifluoroacetate (H-Val-O-TCA x TFA)

2.5 g (4.0 mmol) of Boc-Val-O-TCA (Example 42) is reacted with trifluoroacetic acid/dichloromethane analogously to Example 2. Crystallization from dichloromethane/diisopropyl ether yields 2.58 g (100%) of (2S)-2-amino-3-methyl-butyric acid [11β,21 -dihydroxy-3,20-dioxo-9-fluoro-16α, 17- [(1-methylethylidene) bis(oxy)]-pregna-1,4-dien-21-yl] ester trifluoroacetate.

Example 44

N-(N-(N-(N-((1,1-Dimethyl)ethoxycarbonyl)-L-alanyl)-L-alanyl)-L -prolyl)-L-valine [11β,21-dihydroxy-3,20-dioxo-9-fluoro-16α,17-[(1-methylethylidene) his (oxy)]-pregna-1, 4-dien-21-yl] ester (Boc-Ala-Ala-Pro-Val-O-TCA)

900 mg (1.50 mmol) of H-Val-O-TCA x TFA (Example 43), 500 mg (1.40 mmol) of Boc-Ala-Ala-Pro-OH and 168 mg (1.40 mmol) of N-hydroxybenzotriazole are dissolved in this sequence in 50 ml of dichloromethane, and 300 µl (3.00 mmol) of N-methylmorpholine is added. Then, a solution of 289 mg (1.40 mmol) of dicyclohexylcarbodiimide in 2 ml of dichloromethane is added and stirred for 2 hours at room temperature. Then, it is suctioned off from precipitated urea, the filtrate is concentrated by evaporation and filtered again. Chromatography of this amount of raw material (300 g of silica gel, hexane/acetone 1:1) yields 935 mg (71%) of N-(N-(N-(N-((1,1-dimethyl)ethoxycarbonyl)-L-alanyl) -L-alanyl)-L-prolyl)-L-valine [11β,21-dihydroxy-3,20-dioxo-9-fluoro-16α,17-[(1-methylethylidene)bis(oxy)]-pregna-1,4-dien-21-yl] ester. Repeated crystallization from dichloromethane/diisopropyl ether provides 817 mg of pure product.

Melting point starting from 151° C. decomposition $[\alpha]_D=$ −1° (c=0.26% in chloroform), HPLC: 93–95%, racemic test (GC): D-Ala 3.0% D-Pro 1.9% D-Val<1%.

Example 45

N-(N-(N-(N-(9H-Fluoren-9-yl-methoxycarbonyl)-L-alanyl)-L-alanyl) L-prolyl)-L-valine [11β,21-dihydroxy-3,20- dioxo-9-fluoro-16α,17-(1-methylethylidene)bis(oxy)]-pregna-1,4-dien-21-yl] ester (Fmoc-Ala-Ala-Pro-Val-O-TCA)

485 mg (0.75 mmol) of H-Val-O-TCA x TFA (Example 43), 336 mg (0.70 mmol) of Fmoc-Ala-Ala-Pro-OH and 84 mg (0.70 mmol) of N-hydroxybenzotriazole are dissolved in this sequence in 20 ml of dichloromethane and 155 μl (1.50 mmol) of N-methylmorpholine is added. Then, a solution of 145 mg (0.70 mmol) of dicyclohexylcarbodiimide in 2 ml of dichloromethane is added and stirred for 12 hours at room temperature. Then, it is suctioned off from precipitated urea, the filtrate is concentrated by evaporation and filtered again. Chromatography of this amount of raw material (300 g of silica gel, dichloromethane→dichloromethane/acetone 1:1) yields 215 mg (30%) of N-(N-(N-(N -(9H-fluoren-9-yl-methoxycarbonyl)-L-alanyl)-L-alanyl)-L-prolyl) -L-valine [11β,21-dihydroxy-3,20-dioxo-9-fluoro-16α,17-[(1methyl-ethylidene)bis(oxy)]-pregna-1,4-dien-21-yl] ester, which does not yield any pure product after crystallization from dichloromethane/diisopropyl ether and ethyl acetate/hexane. Also, a second chromatography (100 g of silica gel, hexane/acetone 1:1) is also unsuccessful. The remaining 50 mg is purified by preparative HPLC (Novapak, MeCN/10 mmol of ammonium hydrogen carbonate 60:40).

HPLC: 99.3–99.6%. Racemic test (GC): D-Ala 1.0% D-Pro 0.8% D-Val 3.2%.

Example 46

N-(N-(N-(L-Alanyl)-L-alanyl)-L-prolyl)-L-valine [11β,21-dihydroxy-3,20-dioxo-9-fluoro-16α,17-[(1-methylethylidene)bis(oxy)]-pregna-1,4-dien-21-yl] ester hydrochloride (H-Ala-Ala-Pro-Val-O-TCA x HCl)

131 mg (0.15 mmol) of Boc-Ala-Ala-Pro-Val-O-TCA (Example 44) is dissolved in 1 ml of hydrochloric acid dioxane (4N HCl in dioxane). After 6 hours at room temperature, the solvent is removed i.vac. and the residue is recrystallized from dichloromethane/diisopropyl ether. 115 mg (95%) of N-(N-(N-(L -alanyl)-L-alanyl)-L-prolyl)-L-valine [11β,21-dihydroxy-3,20-dioxo-9-fluoro-16α,17(1-methyl-ethylidene)bis(oxy)]-pregna-1,4-dien-21-yl] ester hydrochloride is obtained.

Racemic test (GC): D-Ala 2.1% D-Pro<1% D-Val 0.8%.

Example 47

N-(N-(N-(N-(Phenylcarbonyl)-L-alanyl)-L-alanyl)-L-prolyl)-L-valine [11β,21-dihydroxy-3,20-dioxo-9-fluoro-16α,17-[(1-methylethylidene)bis(oxy)]-pregna-1,4-dien-21-yl] ester (Bz-Ala -Ala-Pro-Val-O-TCA)

105 mg (0.13 mmol) of H-Ala-Ala-Pro-Val-O-TCA x HCl (Example 46) is dissolved in 3 ml of dichloromethane and 3 ml of triethylamine, mixed with 23 μl (0.20 mmol) of benzoyl chloride and stirred for 8 hours at room temperature. [or working-up, it is washed with 1N HCl and water, dried on sodium sulfate and concentrated by evaporation i.vac. The residue that remains after removal of the solvent i.vac. is directly chromatographed. Gradient chromatography on 50 g of silica gel 60 (dichloromethane →dichloromethane/methanol 95:5) yields 85 mg (76%) of N-(N-(N -(N-(phenylcarbonyl)-L-alanyl)-L-alanyl)-L-prolyl)-L-valine [11β, 21-dihydroxy-3,20-dioxo-9-fluoro-16β,17-(1-methylethylidene)bis(oxy)]-pregna-1,4-dien-21-yl] ester and, after recrystallization, 56 mg (49%) of crystalline pure product from ethyl acetate/hexane.

Biological Data

1. Binding to the Glucocorticoid Receptor

The binding of the substances according to the invention to the rat glucocorticoid receptor is determined by competitive displacement of tritiated dexamethasone from the receptor binding. Different concentrations of the glucocorticoid esters are incubated for 2 hours at 4° C. in the presence of a constant concentration of tritium-labeled dexamethasone with rat thymus cytosol. After the incubation time, the non-protein-bound steroids are adsorbed on activated carbon and the activated carbon is centrifuged off. The radioactivity in the supernatant is used as a measurement for the amount of receptor-bound dexamethasone.

From the measurements, the concentrations of the respective corticoid derivative are calculated, which are necessary to displace 50% of the labeled dexamethasone from the receptor binding. Competition factor (KF) is the quotient of these calculated concentrations for the test substance and that of dexamethasone. The better a compound binds to the receptor, the lower its KF is.

As can be seen from Table 1, the glucocorticoid-oligopeptide-esters according to the invention bind in a considerably inferior manner than the unesterified glucocorticoid framework to the glucocorticoid receptor of the rat thymus. In this respect, they meet the condition of a prodrug.

TABLE 1

Competition Factors in the Cytosolic Rat Thymus-Glucocorticoid Receptor

| Corticoid | Example | Competition Factor [KF] |
|---|---|---|
| 6α-Methylprednisolone-17-propionate | | 0.8 |
| Boc-Val-O-MPP | 1 | 17 |
| Boc-Ala-Ala-Pro-Val-O-MPP | 3 | 5.6 |
| Fmoc-Ala-Ala-Pro-Val-O-MPP | 4 | 100 |
| Ac-Ala-Ala-Pro-Val-O-MPP | 7 | 20 |
| Bz-Ala-Ala-Pro-Val-O-MPP | 8 | 24 |
| Valeroyl-Ala-Ala-Pro-Val-O-MPP | 9 | 7 |
| 6α-Methylprednisolone | | 0.9 |
| Boc-Val-O-MP | 19 | 144 |
| Boc-Ala-Ala-Pro-Val-O-MP | 21 | 56 |
| Fmoc-Ala-Ala-Pro-Val-O-MP | 22 | 220 |
| Hydrocortisone | | 4 |
| Boc-Val-O-HC | 27 | >1000 |
| Fmoc-Ala-Ala-Pro-Val-O-HC | 29 | k.k. [n.c.] |
| Boc-Ala-Ala-Pro-Val-O-FC | 32 | 5 |
| Boc-Ala-Ala-Pro-Val-O-TCA | 44 | 24 |
| Bz-Ala-Ala-Pro-Val-O-TCA | 47 | 10 |

(k.k. = no competition)

2. Cleavage in the Homogenate of Normal Rat Skin

The homogenate of the skin of male rats (0.1 mol/l of phosphate buffer, pH=7.4) is centrifuged for 20 minutes at 10,000 g. The supernatant is adjusted in phosphate buffer to a protein concentration of 3 mg/ml. The test substances in 20 μl of ethanol are added to 1 ml of this homogenate. The final concentration of the corticoid derivatives is approximately 100 μmol/l. The incubation takes place for different periods at 37° C. At the end of incubation, the samples are extracted three times with 3 ml of chloroform. The combined extracts are evaporated to dryness under nitrogen and taken up with 100 μl of ethanol. The ethanolic solutions are mixed with the same volume of water and the saponification products are separated by HPLC (RP 18, acetonitrile/water-gradient, detection 240 nm). The relative hydrolysis rate is indicated in percent of the hydrolysis rate of the 6α-methylprednisolone-17-propionate-21-acetate.

The oligopeptide esters have proven to be less hydrolysis-sensitive than simple carboxylic acid esters (Table 2).

TABLE 2

Unspecific Cleavage of Corticoid-21-Oligopeptide Esters by Esterases of Rat Skin

| Corticoid | Example | Relative Hydrolysis Rate [%] |
|---|---|---|
| 6α-Methylprednisolone-17-propionate-21-acetate | | 100 |
| Boc-Ala-Ala-Pro-Val-O-MPP | 3 | 50 |
| Fmoc-Ala-Ala-Pro-Val-O-MPP | 4 | 4 |
| DPAc-Ala-Ala-Pro-Val-O-MPP | 10 | 6 |
| DPC-Ala-Ala-Pro-Val-O-MPP | 11 | 14 |
| Naphthoyl-Ala-Ala-Pro-Val-O-MPP | 12 | 4 |
| Cinnamoyl-Ala-Ala-Pro-Val-O-MPP | 13 | 5 |
| Cbs-Ala-Ala-Pro-Val-O-MPP | 14 | 6 |
| Cbp-Ala-Ala-Pro-Val-O-MPP | 16 | 3 |
| Pht-Gly-Ala-Ala-Pro-Val-O-MPP | 17 | 49 |
| Fmoc-Ala-Ala-Pro-Val-O-MP | 22 | 6 |
| Boc-Ala-Ala-Pro-Val-O-BMV | 38 | 0 |
| Fmoc-Ala-Ala-Pro-Val-O-BMV | 39 | 0 |

3. Cleavage of Glucocorticoid-21-Oligopeptide Esters by Leukocyte Elastase

Polymorphonuclear granulocytes are isolated from donor blood. The cells are lysed in a density of $10^6$ cells per ml. 1 ml each of the lysate is mixed with 20 µl of ethanolic corticoid solution (5 mmol/l) After 1 hour of incubation at 37° C., the samples are extracted three times with 3 ml of chloroform and worked up as described above for HPLC analysis. The cleavage of the prodrugs according to the invention can be inhibited under these test conditions by the addition of the specific elastase inhibitor MeO-succinyl-Ala-Ala-Pro-Val-chloromethylketone to 90%. Furthermore, the compounds are also hydrolyzed by pure human sputum-elastase (elastin products). These findings suggest a specific cleavage of the prodrugs by elastase.

TABLE 3

Cleavage of Glucocorticoid-21-esters in the Lysate of Human Neutrophilic Granulocytes

| Corticoid | Example | Relative Hydrolysis Rate [%] |
|---|---|---|
| Boc-Ala-Ala-Pro-Val-O-MPP | 3 | 160–190 |
| Fmoc-Ala-Ala-Pro-Val-O-MPP | 4 | 100 |
| Z-Ala-Ala-Pro-Val-O-MPP | 5 | 160–230 |
| Fmoc-Aib-Ala-Ala-Pro-Val-O-MPP | 18 | 130 |
| Fmoc-Ala-Ala-Pro-Val-O-MP | 22 | 370 |
| Boc-Ala-Ala-Pro-Val-O-FC | 32 | 380 |
| Fmoc-Ala-Ala-Pro-Val-O-BMV | 39 | 42 |

Fmoc-Ala-Ala-Pro-Val-O-MPP is used as reference.

4. Local Antiinflammatory Action

The antiinflammatory activity of the corticoid-21-oligopeptide esters is performed in a modified rat ear test according to Tonelli. The modifications are based on changes of irritant solution (4% croton oil, 10% DMSO in ethanol), the type of administration (application of the solution with pipette) and the evaluation of the test 16 hours after administration of the irritant solution. At this time, both the inhibition of the edema by measuring the ear weight and the inhibition of the granulocytic infiltrate by measuring the granulocyte marker myeloperoxidase and leukocyte-elastase in the ear homogenate can be determined. The group size was 6 animals in each case. As can be seen from Table 4, the antiinflammatory activity of the corticoid-21-oligopeptide esters after topical application is comparable to the activity of the homologous corticoid-21-acetates.

TABLE 4

Antiinflammatory Action of Glucocorticoid-21-Esters after Topical Application (Rat Ear Test)

| Corticoid | Concentration | Edema [% inhibition] | Infiltration [% inhibition] |
|---|---|---|---|
| 6α-Methylprednisolone-17-propionate-21-acetate | 0.3 | 67* | 78* |
| | 0.03 | 62* | 45* |
| | 0.003 | 44* | 12 |
| Boc-Ala-Ala-Pro-Val-O-MPP (Example 3) | 0.3 | 81* | 77* |
| | 0.03 | 51* | 43* |
| | 0.003 | 17 | 11 |
| Fmoc-Ala-Ala-Pro-Val-O-MPP (Example 4) | 0.3 | 78* | 66* |
| | 0.03 | 48* | 42* |
| | 0.003 | 30* | 16* |

*Significant inhibition ($p < 0.05$) relative to positive control (application of croton oil without corticoid)

We claim:
1. A glucocorticoid of general formula I

R—Val—O—GC (I), in which

O-GC is the radical of a 21-hydroxycorticoid that has an antiinflammatory action, Val represents a valine radical in the 21-position of the corticoid and R means a hydrogen atom or a hydrocarbon radical with up to 32 carbon atoms that is optionally substituted by hydroxy groups, amino groups, oxo groups and/or halogen atoms and/or interrupted by oxygen atoms, $SO_2$ groups and/or NH groups a salt thereof.

2. A pharmaceutical preparation comprising a glucocorticoid according to claim 1 and a pharmaceutically acceptable carrier.

3. A glucocorticoid of general formula II $$R^1-X^1-X^2-X^3-Val-O-\text{[steroid structure with HO, A, B, }R^6, R^9, R^{16}, R^{17}\text{, =O]} \quad \text{II}$$

in which $R^1$=H, CH=O, (C=O)R", (C=O)OR" or $SO_2$R"

$X^1$–$X^3$=independently of one another, alanine, proline or valine,

A–B=$CH_2$—$CH_2$ or CH=CH $R^6$=H, F, Cl, Me, $R^9$=H, F, Cl, $R^{16}$=H, Me, OH, $R^{17}$=H, OH, O(C=O)R''' or $R^{16}$, $R^{17}$=alkylidenedioxy, in which R" represents a hydrocarbon radical that contains $C_1$–$C_{18}$ and R''' represents a straight-chain a branched-chain $C_1$–$C_{10}$ alkyl, aryl, alkylaryl or $C_1$–$C_3$ alkoxy radical and the alkylidene radical is derived from an aliphatic aldehyde that contains 1–6 carbon atoms, a ketone that contains 3–6 carbon atoms or cyclic ketone or benzaldehyde that contains 5–6 carbon atoms or a salt therof.

4. A pharmaceutical preparation comprising a glucocorticoid according to claim 3 and a pharmaceutically acceptable carrier.

5. A glucocorticoid of general formula I

R—Val—O—GC (I), in which O—GC is the radical of a 21-hydroxycorticoid that has an antiinflammatory action, Val represents a valine radical in the 21-position of the corticoid and R means a hydrogen atom or a hydrocarbon radical with up to 32 carbon atoms that is optionally substituted by hydroxy groups, amino groups, oxo groups and/or halogen atoms and/or interrupted by oxygen atoms, $SO_2$ groups and/or NH groups; or general formula II

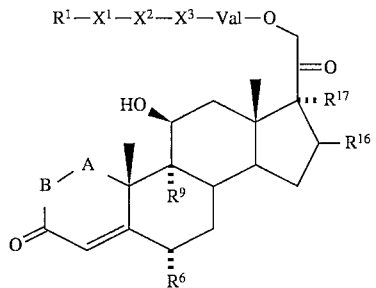

in which $R^1$=H, CH=O, (C=O)R" or $SO_2R"$, $X^1$ and $X^2$=alanine, $X^3$=proline or valine, A—B=$CH_2$—$CH_2$ or CH=CH, $R^6$=H, F, Cl, Me, $R^9$=H, F, Cl, $R^{16}$=H, Me, OH, $R^{17}$=H, OH, O(C=O)R''' or $R^{16}$, $R^{17}$=alkylidenedioxy, in which R" represents a hydrocarbon radical that contains $C_1$–$C_{18}$ and R''' represents a straight-chain or branched-chain $C_1$–$C_{10}$ alkyl, aryl, alkylaryl or $C_1$–$C_3$ alkoxy radical and the alkylidene radical is derived from an aliphatic aldehyde that contains 1–6 carbon atoms, a ketone that contains 3–6 carbon atoms or cyclic ketone or benzaldehyde that contains 5–6 carbon atoms or a salt thereof.

6. A method for treating inflammatory conditions, wherein a glucocorticoid according to claim 5 is administered to a patient in need thereof.

* * * * *